(12) United States Patent
Lawyer

(10) Patent No.: US 6,313,131 B1
(45) Date of Patent: Nov. 6, 2001

(54) METHOD OF KIDNEY TREATMENT

(75) Inventor: Carl H. Lawyer, Mequon, WI (US)

(73) Assignee: Upsher-Smith Laboratories, Inc., Minneapolis, MN (US)

( * ) Notice: Subject to any disclaimer, the term of this patent is extended or adjusted under 35 U.S.C. 154(b) by 0 days.

(21) Appl. No.: 09/505,030

(22) Filed: Feb. 16, 2000

Related U.S. Application Data

(60) Provisional application No. 60/120,097, filed on Feb. 16, 1999.

(51) Int. Cl.$^7$ .................................................. A61K 31/52
(52) U.S. Cl. ......................... 514/263; 514/264; 514/265
(58) Field of Search ...................... 514/263, 264, 514/265

(56) References Cited

U.S. PATENT DOCUMENTS

| | | |
|---|---|---|
| 2,575,344 | 11/1951 | Jones et al. . |
| 4,031,218 | 6/1977 | El-Antably . |
| 4,187,308 | 2/1980 | Franzone et al. . |
| 4,341,783 | 7/1982 | Scheindlin . |
| 4,581,359 | 4/1986 | Ayres . |
| 5,753,641 | 5/1998 | Gormley et al. . |
| 5,891,904 | * 4/1999 | Stief et al. ............................ 514/423 |

OTHER PUBLICATIONS

Kukovetz et al, Arzneimittelforschung, vol. 33, #10, pp. 1450–1454, Oct. 1983.*

Anderson, "The Concept of Uroselectivity," *Eur. Urol.*, 33(Suppl. 2):7–11 (1998).

Bang et al., "Cyclic AMP induces transforming growth factor β2 gene expression and growth arrest in the human androgen–independent prostate carcinoma cell line PC–3," *Proc. Natl. Acad. Sci. USA*, 89 (8):3556–3560 (1992).

Barza, "Anatomical Barriers for Antimicrobial Agents," *Eur. J. Clin. Microbiol. Infect. Dis.*, 12(Suppl. 1):S31–S35 (1993).

Boatman et al., "Pharmacological Evaluation of Ureteral Smooth Muscle, A Technique for Monitoring Ureteral Peristalsis," *Invest. Urol.*, 4(6):509–520 (1967).

Coe et al., "The Pathogenesis and Treatment of Kidney Stones," *N. Engl. J. Med.*, 327(16):1141–1152 (1992).

Edelstein et al., "Chapter 8: Etiology, Pathogenesis, and Management of Renal Failure," *Campbell's Urology*, 7$^{th}$ edition, Walsh et al., eds., W.B. Saunders Co., Philadelphia, Title page, publication page, table of contents, and pp. 315–341 (1998).

Fair et al., "The pH of Prostatic Fluid: A Reappraisal and Therapeutic Implications," *J. Urol.*, 120 (6):695–698 (1978).

Fang et al., "P$_2$—Purinergtic Receptor Agonists Inhibit the Growth of Androgen independent Prostate Carcinoma Cells," *J. Clin. Invest.*, 89(1):191–196 (1992).

Kawabe et al., "Use of an ⊕1–Blocker, YM617, in the Treatment of Benign Prostatic Hypertrophy," *J. Urol.*, 144(4):908–912 (1990).

Kerttula et al., "Theophylline infusion modulates prostaglandin and leukotriene production in man," *Prostaglandins Leukot. Essent. Fatty Acids*, 57(6):555–560 (1997).

Leoni et al., "The Effects of Isoproterenol and Aminophylline on Detrusor Muscle Contractility in an Organ Bath Apparatus," *Invest. Urol.*, 10(6):458–463 (1973).

Martin et al., "Relationship Between the Effects of Alfuzosin on Rat Urethral and Blood Pressures and its Tissue Concentrations," *Life Sci.*, 63(3):169–176 (1998).

Martin et al., "Functional Uroselectivity," *Eur. Urol.*, 33(Suppl. 2):12–18 (1998).

Nadai et al., "Pharmacokinetics and the Effect of Probenecid on the Renal Excretion Mechanism of Diprophylline," *J. Pharm Sci.*, 81(10):1024–1027 (1992).

Oesterling, "Benign Prostatic Hyperplasia—Medical and Minimally Invasive Treatment Options," *N. Engl. J. Med.*, 332(2):99–109 (1995).

Simons et al., "Urinary Excretion of Dyphylline in Humans," *J. Pharm. Sci.*, 68 (10):1327–1329 (1979).

Wein et al., "The Effects of Aminophylline on Ureteral and Bladder Contractility," *Invest. Urol.*, 9(4):290–293 (1972).

Brambilla et al., "Activation of the A$_3$ adenosine receptor affects cell cycle progression and cell growth," *Naunyn–Shmiedeberg's Arch Pharmacol*, Mar. 2000; 361(3):225–34.

Brodie et al., "Activation of the A$_{2A}$ adenosine receptor inhibits nitric oxide production in glial cells," *FEBS Lett.* Jun. 1998; 429(1):139–42.

Conti et al., "The Molecular Biology of Cyclic Nucleotide Phosphodiesterases," *Prog Nucleic Acid Res Mol Biol.* 1999;63:1–38.

Conti, "Phosphodiesterases and cyclic nucleotide signaling in endocrine cells," *Mol Endocrinol.* Sep. 2000;14(9):1317–27.

Granovsky et al., "Identification of the gamma subunit–interacting residues on photoreceptor cGMP phosphodiesterase , PDE6α'," *J. Biol Chem.* Dec. 29, 2000;275(52):41258–62.

(List continued on next page.)

*Primary Examiner*—James H. Reamer
(74) *Attorney, Agent, or Firm*—Mueting, Raasch & Gebhardt, P.A.

(57) ABSTRACT

A method of treating and/or preventing renal dysfunction in a patient, such as renal colic or contrast nephropathy by administering to a patient, a compound of the formula:

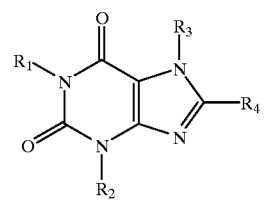

is described herein. Administration of dyphylline in a sustained release oral dosage form is preferred.

20 Claims, No Drawings

OTHER PUBLICATIONS

Hasan et al., "Antagonism of coronary artery relaxation by adenosine $A_{2A}$ –receptor antagonist ZM241385," *J Cardiovasc Pharmacol.* Feb. 2000; 35(2):322–5.

Kotera et al., "Immunohistochemical localization of cGMP-binding cGMP–specific phosphodiesterase (PDE5) in rat tissues," *J Histochem Cytochem.* May 2000;48(5):685–93.

Landells et al., "The role of adenosine receptors in the action of theophylline on human peripheral blood mononuclear cells from healthy and asthmatic subjects," *Br J Pharmacol*, Mar. 2000; 129(6):1140–4.

Lew et al., "Examination of adenosine receptor–mediated relaxation of the pig coronary artery," *Clin Exp Pharmacol Physiol*, May–Jun. 1999; 26(5–6):438–43.

Li et al., "Adenosine $A_{2a}$ receptors increase arterial endothelial cell nitric oxide," *J. Surg Res*, Dec. 1998; 80(2):357–64.

Li et al. "Adenosine enhances nitric oxide production by vascular endothelial cells," *Am J Physiol*, Aug. 1995; 269(2Pt 1):C519–23.

Olanrewaju et al., "Adenosine $A_{2A}$ and $A_{2B}$ receptors in cultured human and porcine coronary artery endothelial cells," *Am J. Physiol Heart Circ Physiol*, Aug. 2000; 279(2):H650–6.

Rump et al., "Adenosine mediates nitric–oxide–independent renal vasodilation by activation of $A_{2A}$ receptors," *J. Hypertens.* Dec. 1999; 17(12 Pt 2):1987–93

Schmeichel et al.,"Methylxanthine bronchodilators potentiate multiple human neutrophil functions," *J. Immunol.* Mar. 1987; 138(6):1896–903.

Schmidt et al. "The Effect of Selective and Non–selective Phosphodieterase Inhibitors on Allergen–and Leukotriene C(4)–Induced Contractions in Passively Sensitized Human Airways," *Br J Pharmacol.* Dec. 2000;131(8):1607–18.

Shneyvays et al., "Induction of apoptosis in cardiac myocytes by an $A_3$ adenosine receptor agonist," *Exp Cell Res.* Sep. 1998;243(2):383–97.

Shneyvays et al., "Induction of apoptosis in rat cardiocytes by $A_3$ adenosine receptor activation and its suppression by isoproterenol," *Exp Cell Res.* May 2000;257(1):111–26.

This Week in Science: from *Science.* Jun. 9, 2000;288(5472):1701.

Walker et al., "Adenosine $A_{2a}$ receptor activation delays apoptosis in human neutrophils," *J Immunol*, Mar. 1997;158(6):2926–31.

Xu et al., "Atomic Structure of PDE4: Insights into Phosphodiesterase Mechanism and Specificity," *Science.* Jun. 9, 2000;288:822–1825.

Yasui et al., "Effects of theophylline on human eosinophil functions: comparative study with neutrophil functions," *J Leukoc Biol.* Aug. 2000;68(2):194–200.

Yasui et al., "Theophylline induces neutrophil apoptosis through adenosine $A_{2A}$ receptor antagonism,"*J Leukoc Biol.* Apr. 2000;67(4):529–35.

Acara et al., "Probenecid inhibition of the renal excretion of dyphylline in chicken, rat and man," *J. Pharm. Pharmacol.*, 39(7):526–530 (1987).

Becker et al., "The effect of the specific phosphodiesterase–IV–inhibitor rolipram on the ureteral peristalsis of the rabbit in vitro and in vivo," *J. Urol.*, 160(3Pt.1):920–925 (1998).

Drescher et al., "Alpha–1 receptor mediated smooth muscle regulation in benign prostatic hyperplasia," *Scand. J. Urol. Nephrol. Suppl.*, 157:33–40 (1994).

Drescher et al., "Smooth Muscle Contractility in Prostatic Hyperplasia: Role of Cyclic Adenosine Monophosphate," *Prostate*, 25(2):76–80 (1994).

Drescher et al., letter to Editor (regarding "Nephrotoxicity from contrast media:attenuation with theophylline," which appeared in *Radioloty*, 195(1):17–22 (1995)), *Radioloty*, 197(2):547–548 (1995).

Drescher, "$Ca^{2+}$ and Cyclic Adenosine Monophosphate Involvement in Radiographic Contrast Medium–induced Renal Vasoconstriction," *J. Vasc. Interv. Radiol.*, 6(5):813–818 (1995).

Erley et al., "Adenosine antagonist theophylline prevents the reduction of glomerular filtration rate after contrast media application," *Kidney Int.*, 45(5):1425–1431 (1994).

Gladstone et al., "The use of theophylline ethylene diamine (aminophylline) for the relief of biliary colic: a preliminary report," *J. Am. Med. Assoc.*, 126(17):1084–1085 (1944).

Katholi et al., "Nephrotoxicity from Contrast Media: Attenuation with Theophylline," *Radiology*, 195(1):17–22 (1995).

King et al., "Purinergic Modulation of Rat Urinary Bladder Detrusor Smooth Muscle," *Gen. Pharmacol.*, 29(4):597–604 (1997).

Kolonko et al., "The nonselective adenosine antagonist theophylline does prevent renal dysfunction induced by radiographic contrast agents," *J. Nephrology*, 11(3):151–156 (1998).

Lawyer et al., "Utilization of intravenous dihydroxypropyl theophylline (dyphylline) in an aminophylline–sensitive patient, and its pharmacokinetic comparison with theophylline," *J. Allergy Clin. Immunol.*, 65(5):353–357 (1980).

May et al., "Effect of probenecid on dyphylline elimination," *Clin. Pharmacol Therapeut.*, 33(6):822–825 (1983).

Morcos et al., "Nephrotoxicity from Contrast Media: Attenuation with Theophylline," letter to Editor (regarding "Nephrotoxicity from contrast media: attenuation with theophylline," which appeared in *Radiology*, 195(1):17–22 (1995)), *Radiology*, 197(2):546–547 (1995).

Morcos et al., "Contrast Media–induced Nephrotoxicity: A New Insight," *Clin. Radiol.*, 52(8):573–574 (1997).

Nolan, "Theophylline option for attenuating contrast media–induced nephrotoxicity in patients on metformin," *Am. J. Health–Syst. Pharm.*, 54(5):587–588 (1997).

Osswald et al., "Therapeutic use of theophylline to antagonize renal effects of adenosine," *Clin. Nephrol.*, 43 (Suppl. 1):S33–S37 (1995).

Quasny, "Metformin, contrast media, and theophylline," *Am. J. Health–Syst. Pharm.*, 54(17):2007–2008 (1997).

\* cited by examiner

METHOD OF KIDNEY TREATMENT

CROSS-REFERENCE TO RELATED APPLICATION

This application claims the benefit of a provisional application filed 16 Feb. 1999, entitled "Method of Kidney Treatment," and having serial number 60/120,097, which is incorporated herein by reference.

FIELD OF THE INVENTION

The present invention relates to a method of treating renal colic and preventing contrast nephropathy in a subject suffering therefrom with an effective amount of dyphylline or an analog thereof.

BACKGROUND

Xanthine is a dioxypurine that is structurally related to uric acid. Xanthine can be represented by the following structure:

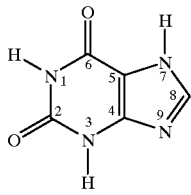

Caffeine, theophylline and theobromine are methylated xanthines. Methylated xanthines such as caffeine and theophylline are typically used for their bronchodilating action in the management of obstructive airways diseases such as asthma. The bronchodilator effects of methylxanthines are thought to be mediated by relaxation of airway smooth muscle. Generally, methylxanthines function by inhibiting cyclic nucleotide phosphodiesterases and antagonizing receptor-mediated actions of adenosine.

Theophylline can be represented by the following structure:

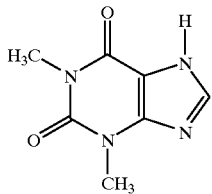

However, when administered intravenously or orally, theophylline has numerous undesired or adverse effects that are generally systemic in nature. It has a number of adverse side effects, particularly gastrointestinal disturbances and CNS stimulation. Nausea and vomiting are the most common symptoms of theophylline toxicity. Moderate toxicity is due to relative epinephrine excess, and includes tachycardia, arrhythmias, tremors, and agitation. Severe toxicity results in hallucinations, seizures, dysrythmias and hypotension. The spectrum of theophylline toxicity can also include death.

Furthermore, theophylline has a narrow therapeutic range of serum concentrations above which serious side effects can occur. The pharmacokinetic profile of theophylline is dependent on liver metabolism, which can be affected by various factors including smoking, age, disease, diet, and drug interactions.

Generally, the solubility of methylxanthines is low and is enhanced by the formation of complexes, such as that between theophylline and ethylenediamine (to form aminophylline). The formation of complex double salts (such as caffeine and sodium benzoate) or true salts (such as choline theophyllinate) also enhances aqueous solubility. These salts or complexes dissociate to yield the parent methylxanthine when dissolved in aqueous solution. Although salts such as aminophylline have improved solubility over theophylline, they dissociate in solution to form theophylline and hence have similar toxicities. However, aminophylline has been reported to be effective in reducing the incidence of contrast nephropathy.

Dyphylline is a covalently modified derivative of xanthine (1,3,-dimethyl-7-(2,3-dihydroxypropl)xanthine. Because it is covalently modified, dyphylline is not converted to free theophylline in vivo. Instead, it is absorbed rapidly in therapeutically active form. Dyphylline has a lower toxicity than theophylline. Dyphylline can be represented by the following structure:

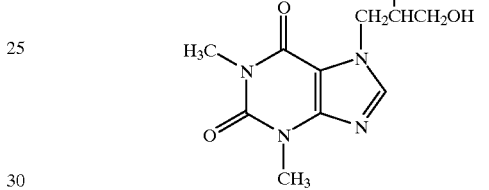

Dyphylline is an effective bronchodilator that is available in oral and intramuscular preparations. Generally, dyphylline possesses less toxic side effects than theophylline.

U.S. Pat. No. 4,031,218 (El-Antably) discloses the use of 7-(2,3-dihydroxypropyl)-1,3-di-n-propylxanthine, a derivative of theophylline, as a bronchodilator. U.S. Pat. No. 4,341,781 (Scheindlin) discloses the use of dyphylline in the treatment of psoriasis and other diseases of the skin by topical administration of dyphylline. U.S. Pat. No. 4,581,359 (Ayres) discloses methods for the management of bronchopulmonary insufficiency by administering an N-7-substituted derivative of theophylline, including dyphylline, etophylline, and proxyphylline.

A kidney stone (also called a bladder stone or cystic calculi) is an abnormal accumulation of mineral salts or crystals that separate from urine and build up on the inner surfaces of the kidney. The medical terminology for kidney stones is nephrolithiasis or renal calculi. A kidney stone can be as small as a grain of sand or as large as a golf ball. Nephrolithiasis has prevalence in the American population of about 5 cases per 1000 persons. Calcium oxalate calculi (73%) are the most common, followed by calcium phosphate and magnesium ammonium phosphate (16%), uric acid (7%) and cystine (1%) calculi. The most common sites of kidney stone impaction are a renal calyx, the ureteropelvic junction, the pelvic brim, and the ureterovesical junction.

Kidney stones may stay in the kidney and grow or may dislodge and try to pass down the narrow ureter into the bladder. About 90% of stones will pass spontaneously within three to six weeks. Most small stones pass within hours or a few days. Other stones must be removed medically. Generally, small stones can pass through the urinary system without causing problems. However, larger stones can block the flow of urine or irritate the lining of the urinary tract. If left untreated, this shut down can lead to permanent loss of finction in that kidney. Even worse, the kidney stone can even rupture the collection system of the kidney and even result in death.

Renal colic (strong kidney pain) results when the stone enters the ureters. These sharp pains may last hours or days. Symptoms include increased urination with pus and blood, pallor, nausea, and vomiting. Sometimes the patient experiences fever and chills.

If a stone will not pass by itself, it can be removed. Extracorporeal Shockwave Lithotripsy (ESWL) is a method of stone treatment where shock waves (non-electrical shocks) are passed through the patient's body. The stone is fragmented and the (smaller) fragments are passed. Ureteroscopy is a technique that involves placing a scope into the urethra, the bladder and then fmally up into the narrow ureters. This scope engages the stone and either fragments it or extracts it. The percutaneous method (PNL) involves placing a scope directly through the skin in the patient's back into the kidney. The stone may then be removed or fragmented through this scope. This technique is generally reserved for larger stones. In open surgery, a doctor actually opens up the kidney and physically takes out the stones.

Aminophylline is known to be effective in relieving biliary colic. Gladstone et al., (1944), *JAMA*, 126:1084–1085.

Injections of radiocontrast agents are another cause of acute decreases in renal function. Contrast associated nephropathy occurs most often in patients with chronic renal insufficiency and diabetes mellitus. Contrast-associated nephropathy is characterized by a significant rise in serum creatinine 1–5 days following intervascular contrast injection. Contrast nephropathy results in significant deterioration of renal finction in many patients. Acute intrarenal vasoconstriction contributes to the acute renal failure due to radiocontrast agents (contrast nephropathy).

Kolonko et al, (1998), *J. Nephrol.*, 11(3):151–6 report that radiocontrast agent induced impairment of renal function can be prevented by giving theophylline before administering the radiocontrast agent. Katholi et al., (1995), *Radiology*, 195(1):17–22 conclude that depression of creatine clearance after administration of contrast medium can be prevented by administration of theophylline.

SUMMARY

The invention provides a method of treating and/or preventing renal dysfunction in a patient, such as renal colic or contrast nephropathy by administering a therapeutic or prophylactic effective amount of dyphylline or a dyphylline analog, or a pharmaceutically acceptable salt thereof to the patient. According to the invention, the compound can be of the formula:

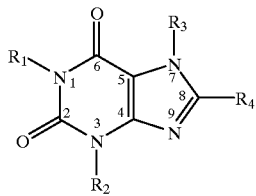

wherein $R_1$ and $R_2$, independently, are hydrogen or a $C_1$–$C_6$ linear or branched alkyl optionally interrupted with a carbonyl. $R_3$ is a $C_1$–$C_8$ alkyl substituted by one or more moieties selected from the group consisting of a hydroxyl, amino, mercapto, dioxolan, carbonyl, and mixtures thereof. $R_4$ is hydrogen; a substituted or unsubstituted aromatic member selected from the group consisting of phenyl, biphenyl, benzyl, or furyl, in which the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro; cyclohexyl or cyclopentyl. Preferably, $R_1$ and $R_2$, are methyl; $R_3$ is dihydroxypropyl; and $R_4$ is hydrogen or a substituted or unsubstituted aromatic member selected from the group consisting of phenyl or benzyl, in which the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro. Most preferred is dyphylline, wherein $R_1$ and $R_2$ are methyl; $R_3$ is 2,3-dihydroxypropyl; and $R_4$ is hydrogen.

DETAILED DESCRIPTION

This invention is directed toward a method of treating or preventing renal diseases such as renal colic and contrast nephropathy by administering an effective amount of dyphylline or a dyphylline analog.

Dyphylline-type Compounds

According to the invention, a dyphylline-type compound includes dyphylline and analogs thereof and can be represented by the following structure:

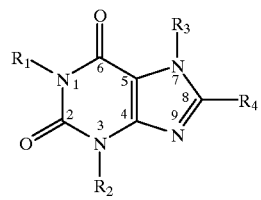

$R_1$ and $R_2$, independently, can be hydrogen or a $C_1$–$C_6$ alkyl optionally interrupted by a carbonyl group. $C_1$–$C_6$ alkyl includes linear or branched species and further includes species that are interrupted in the chain by a carbonyl group. $C_1$–$C_6$ alkyl includes, but is not limited to, methyl, ethyl, n-propyl, isopropyl, n-butyl, isobutyl, sec-butyl, t-butyl, and 5-oxohexyl. Dyphylline-type compounds with large nonpolar substituents at $R_1$ and $R_2$ usually display an enhancement in both the ability to inhibit cyclic nucleotide phosphodiesterases and to antagonize receptor-mediated actions of adenosine. Preferably, $R_1$ and $R_2$ are methyl.

$R_3$ can be a $C_1$–$C_8$ alkyl (preferably a $C_1$–$C_4$ alkyl) substituted by one or more moieties selected from the group consisting of hydroxyl, amino, mercapto, dioxolan, carbonyl, and mixtures thereof. $C_1$–$C_8$ alkyl includes both linear and branched species, including methyl, ethyl, n-propyl, isopropyl, n-butyl, isobutyl, sec-butyl, t-butyl, n-pentyl, isopentyl, neopentyl, n-hexyl, and the like. Examples of suitable substituted alkyl groups include hydroxymethyl, hydroxyethyl, hydroxypropyl, dihydroxypropyl, e.g., 2,3-dihydroxypropyl or 1,3-dihydroxypropyl, 1,3-dioxolan-2-ylmethyl, methanamino, ethanamino, pyrrolidinomethyl, morpholinomethyl, piperidinomethyl, methanethio, ethanethio, and the like. In a preferred embodiment, $R_3$ is dihydroxypropyl. In a most preferred embodiment, $R_3$ is 2,3-dihydroxypropyl.

$R_4$ can be hydrogen; a substituted or unsubstituted aromatic member; or a cycloalkyl, such as cyclohexyl or cyclopentyl. Addition of an aromatic member or a cycloalkyl at $R_4$ usually markedly increases the affinity of the dyphylline-type compound for adenosine receptors, but reduces inhibition of cyclic nucleotide phosphodiesterases. Suitable aromatic members include phenyl, biphenyl, benzyl, and furyl. Suitable substituents on the aromatic ring include $C_1$–$C_4$ alkyl, $C_1$–$C_4$ haloalkyl, $C_1$–$C_4$ alkoxy, $C_1$–$C_4$ alkylthio, halo and nitro. $C_1$–$C_4$ alkyl includes both linear and branched species, including methyl, ethyl, n-propyl, isopropyl, cyclopropyl, n-butyl, isobutyl, sec-butyl, t-butyl, and the like. $C_1$–$C_4$ haloalkyl includes both linear and branched species of $C_1$–$C_4$ alkyl, substituted with chloro, fluoro, bromo and iodo, preferably chloro. $C_1$–$C_4$ alkoxy includes linear or branched species, including, but not limited to, methoxy, ethoxy, n-propoxy, isopropoxy, n-butoxy, isobutoxy, sec-butoxy, t-butoxy, preferably methoxy. $C_1$–$C_4$ alkylthio includes linear or branched species of $C_1$–$C_4$ alkyl, substituted with at least one divalent thio (-S-) grouping including: methylthio, ethylthio, isopropylthio, n-butylthio, and the like. Halo includes chloro, fluoro, bromo, iodo, preferably chloro.

Examples of dyphylline-type compounds include:
7-(2,3-dihydroxypropyl)theophylline (also called dyphylline);
7-(β-hydroxyethyl)theophylline;
7-(pyrrolidinomethyl)theophylline;
7-(2-hydroxypropyl)theophylline;
7-(morpholinomethyl)theophylline;
7-(β-hydroxypropyl)theophylline;
7-(piperidinomethyl)theophylline;
7-[2-(diethylamino)ethyl]theophylline (also called metescufylline);
7-(1,3-dioxolan-2-ylmethyl)theophylline (also called doxofylline);
theophylline-7-acetate (also called acefylline); and
1-(5-oxohexyl)-3,7-dimethylxanthine (also called pentoxyfylline).

The preferred compounds are pentoxyfylline and dyphylline. Pentoxyfylline is water soluble and excretion is almost totally urinary. The main biotransformation product is metabolite V (1-(3-carboxypropyl)-3,7-dimethylxanthine). The most preferred compound is dyphylline.

Dyphylline-type compounds are either commercially available or can be synthesized by methods known to those skilled in the art. For example, a method of preparing dyphylline can be found in U.S. Pat. No. 2,575,344, the disclosure of which is incorporated herein by reference.

Also included within the scope of this invention are pharmaceutically acceptable salts of the dyphylline-type compounds shown above. The salts are acid addition salts and can be formed where a basic group is present on the dyphylline-type compound. Where a basic substituent is present, suitable acids for salt formation include, but are not limited to, hydrochloric, sulfuric, phosphoric, acetic, citric, oxalic, malonic, salicylic, malic, gluconic, fumaric, succinic, ascorbic, maleic, and methanesulfonic. The salts are prepared by contacting the dyphylline-type compound with a sufficient amount of the desired acid to produce a salt. The dyphylline-type compound may be regenerated by treating the salt form with a base. The salt forms differ from the dyphylline-type compounds in certain physical properties such as solubility in polar solvents, but the salts are otherwise equivalent for purposes of this invention.

The compounds of the invention can exist in unsolvated as well as solvated forms, including hydrated forms. In general, the solvated forms, including hydrated forms are equivalent to the unsolvated forms for the purposes of this invention.

Formulations

The dyphylline-type compounds can be administered in a wide variety of oral, intravenous and intramuscular dosage forms, preferably the dyphylline-type compound is administered orally, most preferably the dyphylline-type compound is administered orally in a sustained release formulation. It will be obvious to those skilled in the art that the dosage forms may comprise as the active component, either a dyphylline-type compound or a corresponding pharmaceutically acceptable salt thereof. The formulations of the invention further comprise a pharmacologically acceptable carrier. As used herein, "pharmacologically acceptable" means that the carrier is compatible with the other ingredients of the formulations and not deleterious to the recipient.

Pharmaceutically acceptable carriers are known to those of skill in the art and include both solid or liquid carriers. Preferably, the dyphylline-type compound is prepared in a sustained release solid preparation. Solid preparations include powders, tablets, dispersible granules, capsules, and cachets. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the fmely divided active compound. In the tablet, the active compound is mixed with carrier having the necessary binding properties in suitable proportions and compacted in the shape and size desired. The powders and tablets preferably contain from 5 to 10 to about 80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Alternately, the dyphylline-type compound can be included in a liquid preparation. Liquid preparations include solutions, suspensions and emulsions. For example, water or water-propylene glycol solutions for parenteral injection. Such solutions are prepares so as to be acceptable to biological systems (isotonicity, pH, etc.). Liquid preparations can also be formulated in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing finely divided active component in water with viscous material, i.e., natural or synthetic bums, resins, methyl cellulose, sodium carboxymethyl cellulose, and other well-known suspending agents.

For medical use, the amount of dyphylline-type compound or pharmacologically acceptable salt thereof required to achieve a therapeutic effect will vary with the particular compound and the route of administration. The half-life of dyphylline-type compounds in normal adults is from about 2 to about 3 hours, and total body clearance is about 150 to 200 ml/kg-hr, although renal clearance can be reduced in patients with impaired renal function. Due to the relatively brief half-life in humans, dyphylline-type compounds must be given frequently or in high doses to achieve clinical utility. Thus, a preferred alternate is administration using a sustained release formulation.

A suitable dose of a dyphylline-type compound or pharmacologically acceptable salt thereof is about 200 mg to about 2500 mg, administered every 4 to 6 hours, more preferably, about 15 mg/kg, administered orally about every 6 hours. Preferably, the dyphylline-type compound is administered in a sustained release formulation as a tablet or capsule. Preferably, the dyphylline-type compound is administered in a sustained release formulation that releases about 90% to about 100% of the dyphylline-type compound over a twelve-hour period.

Sustained release formulations and methods of preparing them are known to those of skill in the art. Generally, a sustained release formulation is a preparation that releases the active component over a desired period of time after administration. Typically, a sustained release formulation is prepared by applying a biodegradable, bioerodible or bioabsorbable polymeric formulation that is biocompatible on the surface of the active component. Examples of polymeric formulations for sustained release formulations include, but are not limited to, hydroxypropylnethylcellulose (HPMC), hydrogenated vegetable oil (HVO), and ethylcellulose.

The term "biodegradable" means that the polymeric formulation degrades over time by the action of enzymes, by hydrolytic action and/or by other similar mechanisms in the human body. By "bioerodible," it is meant that the polymeric formulation erodes or degrades over time due, at least in part, to contact with substances found in the surrounding tissue fluids or cellular action. By "bioabsorbable," it is meant that the polymeric formulation is broken down and absorbed within the human body, for example, by a cell or tissue. "Biocompatible" means that the polymeric formulation does not cause substantial tissue irritation or necrosis.

The formulations may conveniently be presented in unit dosage form and may be prepared by any of the methods well known in the art of pharmacy. In unit dosage form, the preparation is subdivided into unit doses containing appropriate quantities of the active component. The unit dosage form can be a packaged preparation, the package containing discrete quantities of preparation, for example, packeted tablets, capsules, or powders in vials or ampoules. The unit dosage form can also be a capsule, cachet, tablet itself or it can be the appropriate number of any of these packaged forms.

Method of Treatment

Dyphylline-type compounds are well suited for clinical use in the symptomatic treatment of renal dysfunction such as renal colic and contrast nephropathy. Dyphylline-type compounds display functional uroselectivity, meaning the dyphylline-type compounds preferentially act on the lower urinary tract rather than the vasculature or the central nervous system.

Whereas a dose of theophylline is generally metabolized by the liver before being excreted in the urine (only about 10% is unchanged), a dose of a dyphylline-type compound is excreted mostly unchanged in the urine (about 83+/−5% is unchanged). Thus, theophylline is present in urine in very low concentrations. In contrast, dyphylline-type compounds undergo rapid and immediate renal excretion and are found at very high concentrations in the urine. Due to their high concentration in urine, dyphylline-type compounds relax bladder smooth muscle at a much lower blood and systemic levels than theophylline. Furthermore, dyphylline-type compound pharmacokinetics and plasma levels are not influenced by various factors that affect liver function and hepatic enzyme activity, such as smoking, age, congestive heart failure, or concomitant use of drugs which affect liver function.

Renal Colic

Rapid renal excretion of dyphylline-type compounds produces high local concentrations of the dyphylline-type compound at the site of stone impaction in the ureter. The dyphylline-type compound produces diuresis and relaxation of ureteral smooth muscle. Thus, treatment of renal colic with dyphylline-type compounds allows passage of larger stones than would pass without treatment. Dyphylline-type compounds also relieve ureteral spasm due to any Demerol, morphine, or codeine administered. Thus, the intensity of pain due to renal colic diminishes following administration of a dyphylline-type compound.

Contrast Nephropathy

According to the method of the invention, a dyphylline-type compound is administered before intravenous contrast is administered to prevent development of contrast nephropathy. Specifically, oral administration of a dyphylline-type compound at a dose of about 200 mg to about 2500 mg, about 15 minutes to about 60 minutes; more preferably about 15 mg/kg, about 30 minutes before intravenous contrast is administered can prevent development of contrast nephropathy. Alternatively, about 200 mg to about 2500 mg, of the dyphylline-type compound can be administered orally about 1 hour to about 3 hours before intravenous contrast is administered.

The rapid renal excretion of dyphylline-type compounds produces high local concentration of the dyphylline-type compound at key sites within the renal parenchyma. The dyphylline-type compound produces diuresis and rapid excretion of the contrast material, thus preventing the contrast material from achieving nephrotoxic concentrations within the renal parenchyma. Dyphylline-type compounds also relieve vascular spasms within the renal parenchyma to prevent contrast nephropathy, even at high doses of contrast media.

The following examples illustrate formulations for use in the method of the invention.

EXAMPLES

EXAMPLE 1

A polygel tablet sustained release formulation for use in the method of the invention is prepared by spraying a povidone/water solution in a fluid bed. The material in the fluid bed is then dried and passed through a mill for sizing. Silicon dioxide and magnesium stearate are combined with the dried material, which is then compressed into tablet form. The percentage of each constituent in the formulation and milligrams per tablet are shown in Table 1, below. The polygel tablet provides 90–100% delivery of dyphylline at 12 hours.

TABLE 1

Polygel Tablet, 12 hour Dyphylline

| MATERIAL | PERCENT | MG/TABLET |
| --- | --- | --- |
| Dyphylline | 75.5 | 400 |
| Hydroxypropylmethylcellulose, USP | 18.0 | 95 |
| Povidone, USP | 6.0 | 32 |
| Silicon Dioxide, NF | 0.3 | 2 |
| Magnesium Stearate, NF | 0.2 | 1 |
| Total | 100.0 | 530 |

Example 2

A sustained release hydrogenated vegetable oil (HVO) tablet for use in the method of the invention is prepared by spraying melted vegetable oil onto dyphylline and allowing the oil to cool. Silicon dioxide and magnesium stearate are combined with the dyphilline/oil mixture, which is then compressed into tablet form. The percentage of each constituent in the formulation and milligrams per tablet are shown in Table 2, below. The HVO tablet provides 90–100% delivery of dyphylline at 12 hours.

TABLE 2

HVO Tablet, 12 hour Dyphylline

| MATERIAL | PERCENT | MG/TABLET |
|---|---|---|
| Dyphylline | 73.0 | 400 |
| Hydrogenated Vegetable Oil, NF | 26.0 | 142 |
| Silicon Dioxide, NF | 0.3 | 2 |
| Magnesium Stearate, NF | 0.7 | 4 |
| Total | 100.0 | 548 |

Example 3

A sustained release formulation of solvent coated beads for use in the method of the invention is prepared by spraying an ethylcellulose/solvent solution onto dyphilline in a fluid bed. The material in the fluid bed is dried and passed through a screen for sizing. Microcrystalline cellulose, silicon dioxide and magnesium stearate are combined with the material, which is then compressed into a tablet. The percentage of each constituent in the formulation and milligrams per tablet are shown in Table 3, below. The tablet provides 90–100% delivery of dyphylline at 12 hours.

TABLE 3

Solvent Coated Beads - Tablet, 12 hour Dyphylline

| MATERIAL | PERCENT | MG/TABLET |
|---|---|---|
| Dyphylline | 71.1 | 400 |
| Ethylcellulose, USP | 19.0 | 107 |
| Microcrystalline Cellulose, NF | 9.0 | 51 |
| Croscarmellose Sodium, NF | 0.5 | 3 |
| Sorbitan Monooleate, NF | 0.4 | 2 |
| Total | 100.0 | 563 |

Example 4

A sustained release formulation for the method of the invention is prepared by spraying an ethylcellulose/solvent solution onto dyphilline in a fluid bed. The material in the fluid bed is dried and passed through a screen for sizing. Sorbitan monooleate and magnesium stearate are combined with the material, which is then filled into a capsule. The percentage of each constituent in the formulation and milligrams per capsule are shown in Table 4, below. The capsule provides 90–100% delivery of dyphylline at 12 hours.

TABLE 4

Solvent Coated Beads - Size "0" Capsule, 12 hour Dyphylline

| MATERIAL | PERCENT | MG/CAPSULE |
|---|---|---|
| Dyphylline | 78.4 | 400 |
| Ethylcellulose, USP | 21.0 | 107 |
| Sorbitan Monooleate, NF | 0.4 | 2 |
| Magnesium Stearate, NF | 0.2 | 1 |
| Total | 100.0 | 510 |

Patents, patent applications, and publications cited herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. A method of treating renal colic in a subject, comprising: administering to the subject in need thereof, a therapeutic effective amount of a compound of the formula:

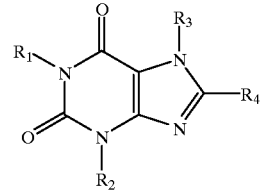

wherein $R_1$ and $R_2$, independently, are hydrogen or a $C_1$–$C_6$ linear or branched alkyl optionally interrupted by a carbonyl;

$R_3$ is a $C_1$–$C_8$ alkyl substituted by one or more moieties selected from the group consisting of hydroxyl, amino, mercapto, dioxolan, carbonyl and mixtures thereof; and $R_4$ is hydrogen; a substituted or unsubstituted aromatic member selected from the group consisting of phenyl, biphenyl, benzyl, and furyl, wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro; or a cycloalkyl selected from the group consisting of cyclohexyl and cyclopentyl; or a pharmaceutically acceptable acid addition salt thereof, in a unit dosage form.

2. The method of claim 1, wherein $R_1$ and $R_2$ are methyl.

3. The method of claim 1, wherein $R_3$ is a $C_1$–$C_8$ alkyl substituted by one or more hydroxyl groups.

4. The method of claim 1, wherein $R_4$ is a substituted or unsubstituted aromatic member selected from group consisting of phenyl, and benzyl, wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro.

5. The method of claim 1, wherein $R_1$ and $R_2$ are methyl; $R_3$ is a $C_1$–$C_4$ alkyl substituted by one or more hydroxyl groups; and $R_4$ is hydrogen.

6. The method of claim 1, wherein $R_1$ and $R_2$ are methyl; $R_3$ is dihydroxypropyl; and $R_4$ is hydrogen.

7. The method of claim 1, wherein $R_1$ and $R_2$ are methyl; $R_3$ is 2,3-dihydroxypropyl; and $R_4$ is hydrogen.

8. The method of claim 1, wherein the compound is administered orally.

9. The method of claim 1, wherein the compound is administered in combination with a pharmaceutically acceptable carrier.

10. The method of claim 1, wherein the compound is administered in a sustained release carrier.

11. A method of preventing contrast nephropathy in a subject, comprising: administering to the subject in need thereof, a prophylactically effective amount of a compound of the formula:

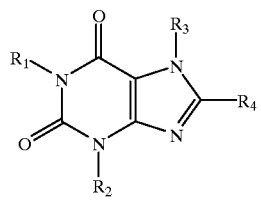

wherein $R_1$ and $R_2$, independently, are hydrogen or a $C_1$–$C_6$ linear or branched alkyl optionally interrupted by a carbonyl;

$R_3$ is a $C_1$–$C_8$ alkyl substituted by one or more moieties selected from the group consisting of hydroxyl, amino, mercapto, dioxolan, carbonyl and mixtures thereof; and $R_4$ is hydrogen; a substituted or unsubstituted aromatic member selected from the group consisting of phenyl, biphenyl, benzyl, and furyl, wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro; or a cycloalkyl selected from the group consisting of cyclohexyl and cyclopentyl; or a pharmaceutically acceptable acid addition salt thereof, in a unit dosage form.

12. The method of claim 11, wherein $R_1$ and $R_2$ are methyl.

13. The method of claim 11, wherein $R_3$ is a $C_1$–$C_8$ alkyl substituted by one or more hydroxyl groups.

14. The method of claim 11, wherein $R_4$ is a substituted or unsubstituted aromatic member selected from group consisting of phenyl, and benzyl, wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro.

15. The method of claim 11, wherein $R_1$ and $R_2$ are methyl; $R_3$ is a $C_1$–$C_4$ alkyl substituted by one or more hydroxyl groups; and $R_4$ is hydrogen.

16. The method of claim 11, wherein $R_1$ and $R_2$ are methyl; $R_3$ is dihydroxypropyl; and $R_4$ is hydrogen.

17. The method of claim 11, wherein $R_1$ and $R_2$ are methyl; $R_3$ is 2,3-dihydroxypropyl; and $R_4$ is hydrogen.

18. The method of claim 11, wherein the compound is administered orally.

19. The method of claim 11, wherein the compound is administered in combination with a pharmaceutically acceptable carrier.

20. The method of claim 19, wherein the compound is administered in a sustained release carrier.

* * * * *